(12) United States Patent
Frye, Jr.

(10) Patent No.: US 7,785,373 B2
(45) Date of Patent: Aug. 31, 2010

(54) PROSTHETIC KNEE AND LEG ASSEMBLY FOR USE IN ATHLETIC ACTIVITIES IN WHICH THE QUADRICEPS ARE NORMALLY USED FOR SUPPORT AND DYNAMIC FUNCTION

(76) Inventor: Todd Jarem Frye, Jr., P.O. Box 190, Amity, OR (US) 97101

( * ) Notice: Subject to any disclaimer, the term of this patent is extended or adjusted under 35 U.S.C. 154(b) by 0 days.

(21) Appl. No.: 11/994,118

(22) PCT Filed: Jun. 27, 2006

(86) PCT No.: PCT/US2006/025113
§ 371 (c)(1),
(2), (4) Date: Aug. 21, 2008

(87) PCT Pub. No.: WO2007/002734
PCT Pub. Date: Jan. 4, 2007

(65) Prior Publication Data
US 2009/0037000 A1 Feb. 5, 2009

(51) Int. Cl.
*A61F 2/64* (2006.01)
*A61F 2/68* (2006.01)
(52) U.S. Cl. .......................................... 623/45; 623/46

(58) Field of Classification Search ............. 623/39–46
See application file for complete search history.

(56) References Cited
U.S. PATENT DOCUMENTS

| 5,904,721 A | 5/1999 | Henry et al. |
| 6,673,117 B1 * | 1/2004 | Soss et al. ..................... 623/24 |
| 6,852,131 B1 | 2/2005 | Chen et al. |

* cited by examiner

*Primary Examiner*—Bruce E Snow
(74) *Attorney, Agent, or Firm*—Angus C. Fox, III (57) ABSTRACT

The present invention provides a new prosthetic knee and lower leg device that enables an above-the-knee amputee to participate in demanding athletic activities in which the quadricep muscles are used extensively for support and dynamic function. The prosthetic device includes a residual thigh attachment plate that is pivotally coupled to a shin frame. An adjustable suspension strut is coupled to both the residual thigh attachment plate and the shin frame. The functional length of the strut can be adjusted, as can be the lower mounting position thereof. The prosthetic device can be adjusted with regard to functional characteristics, performance settings, and "home position" angles of the knee. The extent of adjustability enables the user to adapt the device for different levels of aggressiveness, different activities and different circumstances, and also allows the device to be adapted to users of different weights and size.

12 Claims, 7 Drawing Sheets

Control Unit

FIG. 6

Control Unit

FIG. 7

PROSTHETIC KNEE AND LEG ASSEMBLY FOR USE IN ATHLETIC ACTIVITIES IN WHICH THE QUADRICEPS ARE NORMALLY USED FOR SUPPORT AND DYNAMIC FUNCTION

BACKGROUND OF THE INVENTION

1. Field of the Invention

This invention relates generally to prosthetic devices and, more particularly, to a prosthetic knee and lower leg assembly which enables an individual, who has had a leg amputation between the hip and knee joints, to participate in demanding athletic activities, such as telemark skiing, alpine skiing, cross-country skiing, water skiing, snow boarding, wake boarding, surfing, skate boarding, wind surfing, rock climbing, ice climbing, roller blading and ice skating, in which the quadriceps are ordinarily used extensively for support and dynamic function.

2. History of the Prior Art

A prosthetic device incorporating a joint for articulation of the knee is an essential element of an artificial leg prosthesis called an "above the knee", that is to say which has a foot, an ankle, a lower leg portion (hereinafter called a "leg"), a knee and a socket for receiving the stump of the thigh.

Relative movement of the upper part of the prosthetic device (supporting the socket) with respect to the leg may be controlled using one or a combination of the many known prior art techniques.

The basic function that an above the knee must perform is that of hingeable movement at the knee joint. Damping of the movement is typically provided as the patient steps forward on the prosthesis. As the leg moves behind the patient, energy stored during the damping step is released for propulsion. Damping and propulsion is generally provided through the use of springs, hydraulic or pneumatic cylinders, or by some combination of these devices.

The patient can perform a balancing movement with this type of prosthesis. If this movement is controlled in an appropriate manner, the ability to walk in a relatively natural way can thus be restored.

U.S. Pat. No. 6,852,131 to Chen, et al. discloses an artificial knee joint that includes a joint seat, a support frame, a hydraulic device, a push rod, and a biasing member. The joint seat has a joint body and a rotatable member connected pivotally to the joint body and connected fixedly to a residual thigh. The support frame is connected rotatably to the joint body, and is connectedly fixed to a prosthetic lower leg. The push rod is movable relative to the joint body between an extended position, where a free end of the rotatable member is spaced apart from the joint body to align the lower leg with the thigh, and a retracted position, where the free end of the rotatable member abuts against the joint body. The biasing member biases the push rod to the extended position.

U.S. Pat. No. 5,904,721 to Henry, et al. discloses a prosthetic device having a pneumatic device for knee articulation formed of an upper part adapted to support a socket element for a stump of a thigh, and a lower part intended to receive a tube extended by an ankle and foot. The two parts are connected to each other by an assembly of pivoted links forming a deformable prism. Movement of the two parts between two stable positions of complete extension and flexure, about the variable axis of rotation defined by these connections, is controlled by a pneumatic cylinder having an upper chamber and a lower chamber separated by a piston and communicating with each other by an air duct with adjustable flow.

Many sports, such as telemark skiing, alpine skiing, cross-country skiing, water skiing, snow boarding, wake boarding, surfing, wind surfing, rock climbing, ice climbing, roller blading and ice skating require that the participant maintain flexure of the knee joints for extended periods in order to absorb shocks and provide propulsion. The muscles known as the quadriceps enable participants to maintain a bent knee position so that the legs can act as shock absorbers and provide propulsion, as needed. One of the problems associated with conventional above-the-knee prosthetic devices is that, in order to simulate a normal walking or running gait, they are not designed to provide vertical support for the wearer in a bent knee position. Instead of providing support, they collapse to a configuration of complete flexure and must be manually returned to the extended position.

SUMMARY OF THE INVENTION

The present invention provides a new prosthetic knee and lower leg device that enables an above-the-knee amputee to participate in demanding athletic activities in which the quadricep muscles are used extensively for support and dynamic function. The prosthetic device can be adjusted with regard to functional characteristics, performance settings, and "home position" angles of the knee. The extent of adjustability enables the user to adapt the device for different levels of aggressiveness, different activities and different circumstances, and also allows the device to be adapted to users of different weights and size. The product is not designed, nor does it function well, as a walking or running leg. Thus, it is intended as an interchangeable component meant to be switched back and forth with the normal walking prosthetic device when the need for such an athletic device arises.

The new prosthetic knee and lower leg device includes residual thigh attachment plate that is pivotally coupled to a shin frame with a first titanium axle passing through both the residual thigh attachment plate and the shin frame that rides in sealed needle bearing assemblies. The shin frame, which functions as a lower leg piece, is machined from a solid aluminum billet. A suspension strut, which functions as the amputee's missing quadriceps, is coupled to the residual thigh attachment plate with a second titanium axle and to the shin frame with an adjustable-height trunnion. The first and second titanium axles are axially spaced from one another. The suspension strut has a generally cylindrical main body with a threaded lower portion. An internally-threaded lower spring retention collar engages the threaded lower portion and can be axially rotated to raise or lower it height with respect to the main body, thereby adjusting the amount of tension on a coil spring, which fits over the cylindrical main body. A trunnion mount is also threaded and engages the threaded lower portion. By adjusting the position of the trunnion mount with respect to the cylindrical main body, the distance between the trunnion and the second titanium axle can be varied. By adjusting this distance, the angle that the residual thigh attachment plate makes with the shin frame can be changed. The shorter the distance, the more bent the knee. The can be installed in one of three locations in the shin frame. The middle location corresponds to a normal location. When fixed to the rear location, the control unit functions much like a compound bow, becoming less forceful at full compression, but still ready to spring back into action. This position makes it easier for a telemark skier to stay in a turn position on steeper terrain in which his gravitational pull is not placed directly above the knee as it is on flat ground. In the front position, compression over the full range is much more linear giving constant tension and full rebound throughout the range of motion. This works well for activities such as snow boarding and surfing in which the user must have a stable knee at all times but be able to absorb shock and move dynamically.

DETAILED DISCLOSURE OF THE INVENTION

The invention will now be described with reference to the included drawing FIGS. 1 through 7.

Referring now to FIGS. 2, 3, 4 and 5, the new prosthetic knee and lower leg device includes a shin frame 216 that is pivotally coupled to a residual thigh attachment plate 202 with an artificial knee joint formed by a first titanium axle 208 which passes through the residual thigh plate 202 and extends into opposite sides of the shin frame 216. The residual thigh plate 202 has recesses on each side thereof, each of which houses a sealed needle bearing assembly 246. The first titanium axle 208 is secured on one end by a first set screw 238. The needle bearing assemblies 246 enable the residual thigh plate 202 to rotate about the first titanium axle 208. The inner race of each needle bearing assembly 246 remains stationary with respect to the first titanium axle 208, and the outer race of each needle bearing assembly 246 remains stationary with respect to the residual thigh attachment plate 202. The needle bearing rotate about the inner race and within the inner race of each bearing assembly 246 as the residual thigh attachment plate pivots with respect to the shin frame 216. The first titanium axle 208, along with the sealed needle bearing assemblies 246, forms an artificial knee joint.

Still referring to FIGS. 2, 3, 4 and 5, the shin frame is preferably machined from a solid aluminum billet. An upper portion of the shin frame 216 has a pair of spaced-apart coaxial apertures within which the first titanium axle 208 installs. The shin frame 216 also has a pair of spaced-apart coaxial threaded apertures within which titanium stop bolts 234 install from inside the shin frame 216. The titanium stop bolts 234 limit the angular deflection of the residual thigh attachment plate 202 about the first titanium axle 208.

Figure 4:
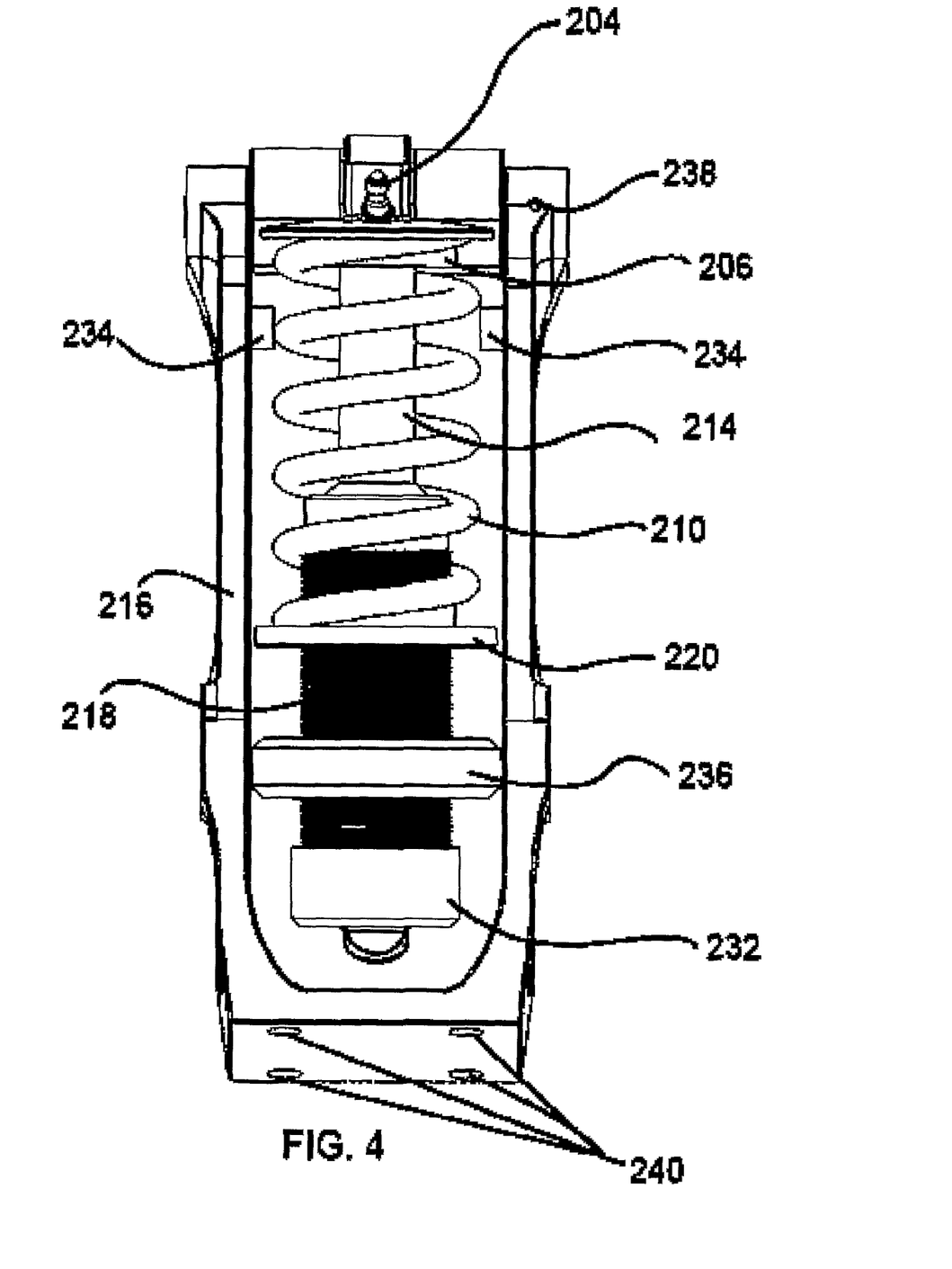
FIG. 4 is an isometric rear view of the invention.

Referring specifically to FIG. 4, the bottom of the shin frame 216 is equipped with four threaded apertures 240 in a square pattern. A prosthetic ankle 104 attaches to the four threaded apertures 240 with threaded fasteners (not shown). A prosthetic foot 106 conventionally attaches to the prosthetic ankle 104.

Figure 1:
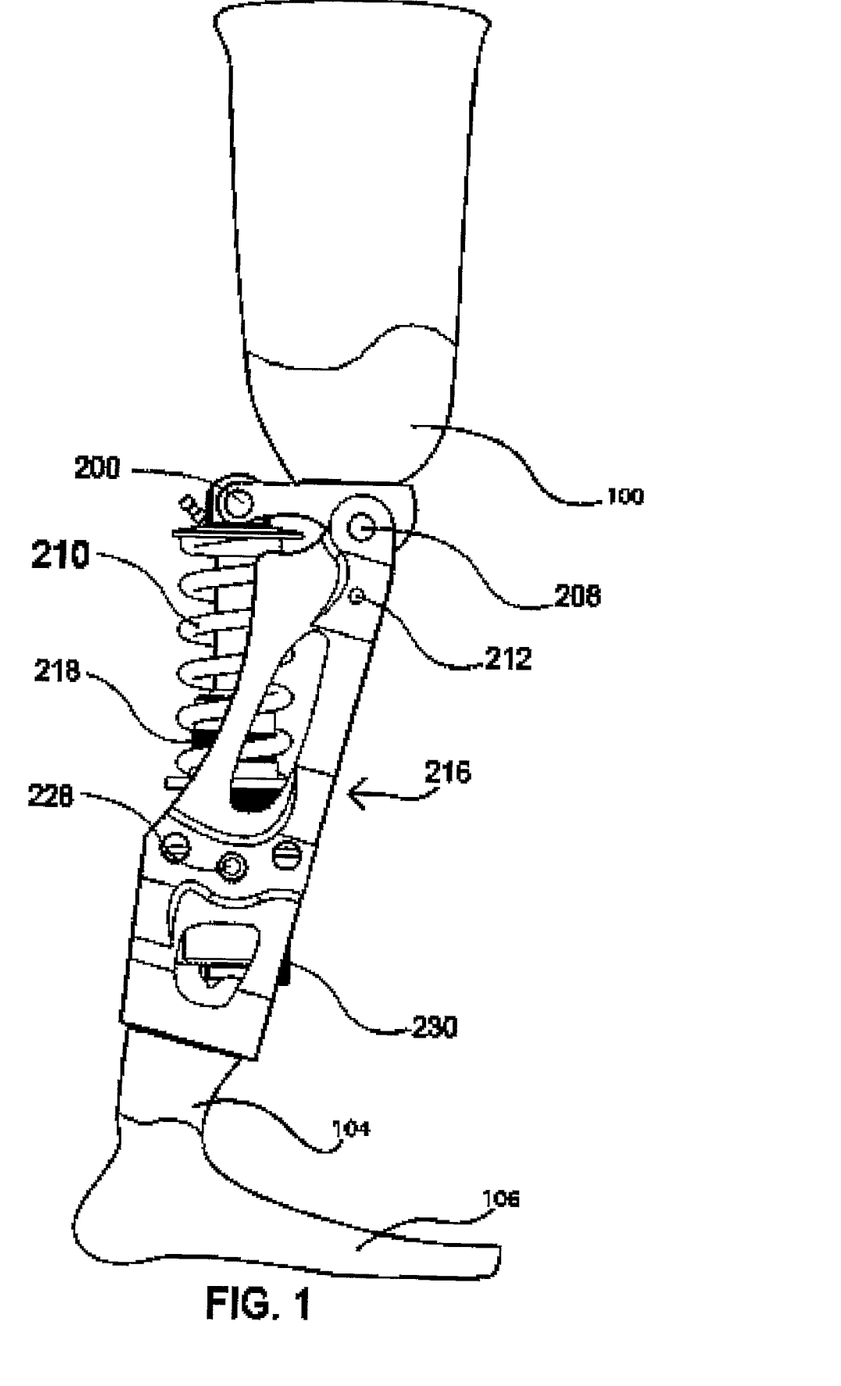
FIG. 1 is a side view of the invention in place as it would fit with the additional futures of the residual thigh socket, ankle and foot components attached to the invention.
Figure 2:
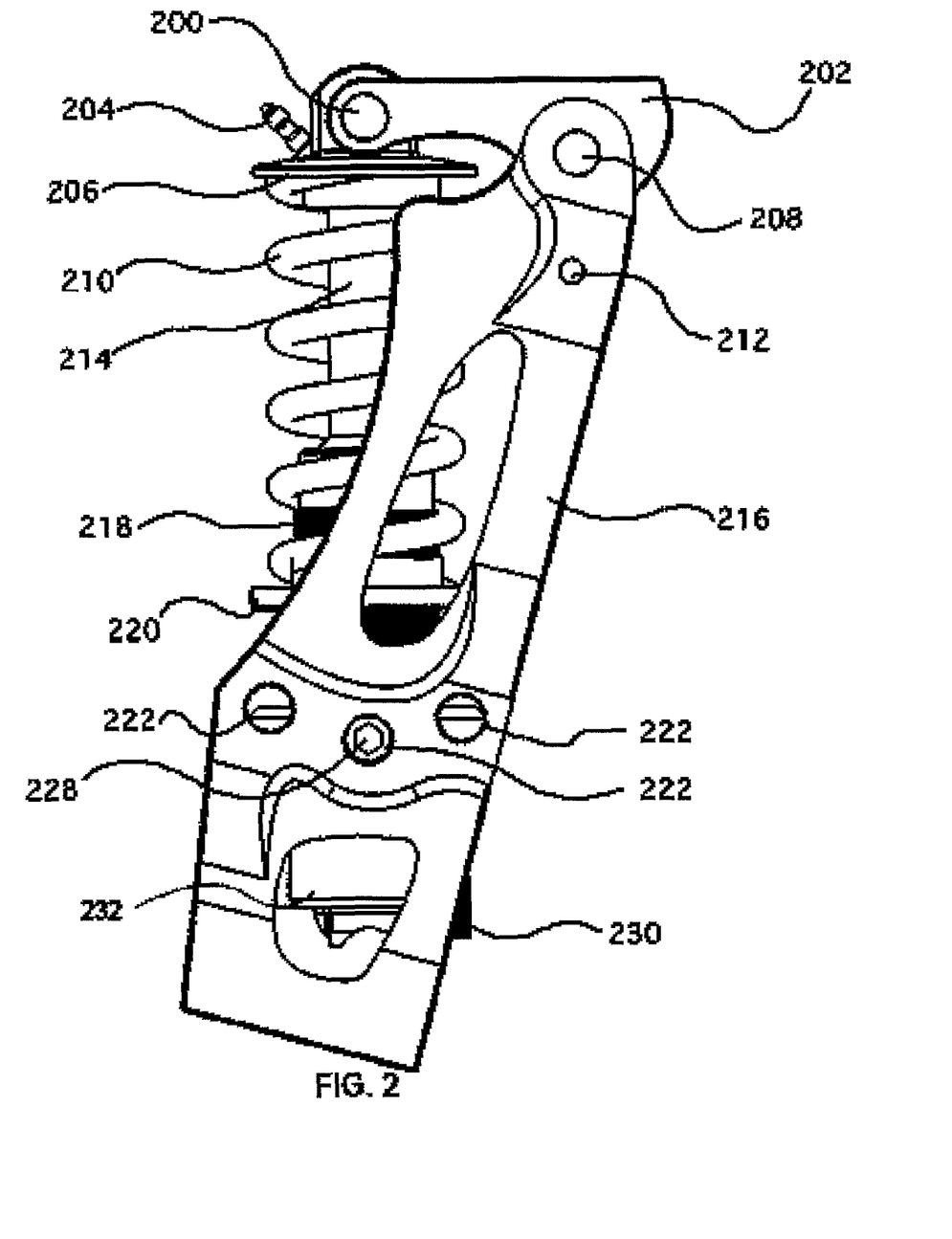
FIG. 2 is an isometric side view of the prosthetic knee invention.
Figure 3:
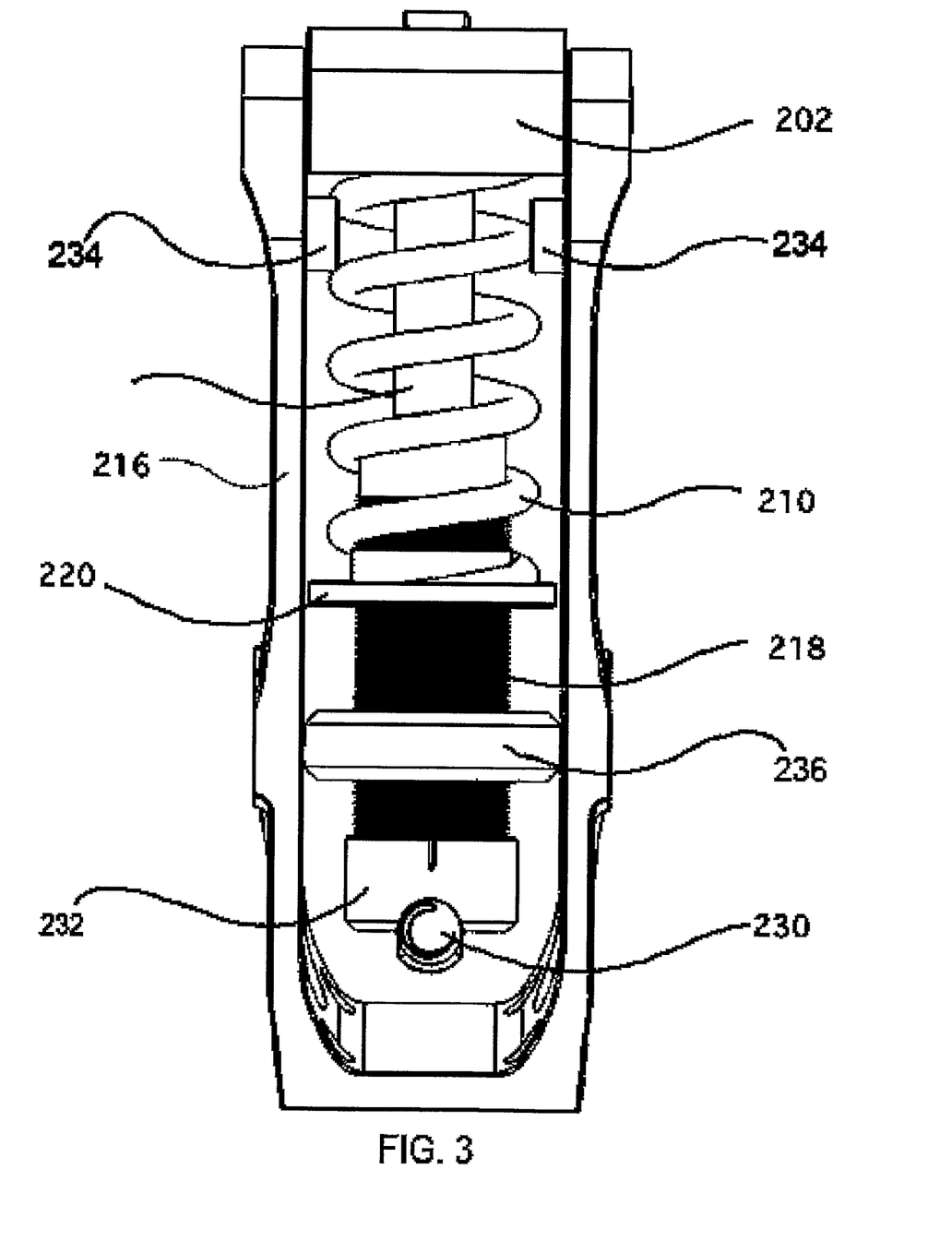
FIG. 3 is an isometric front view of the prosthetic knee invention.
Figure 5:
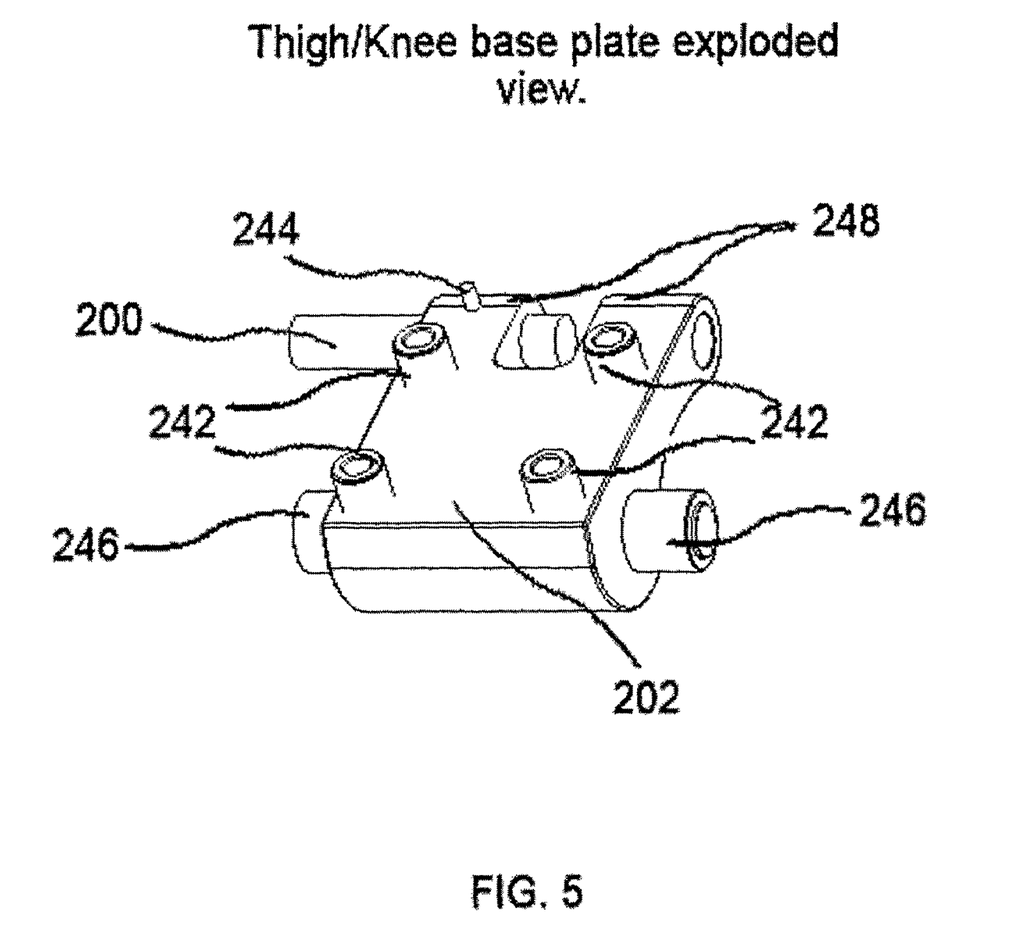
FIG. 5 is an exploded view of the thigh/knee plate component and it's comprising parts.

Referring now to FIG. 1 and FIG. 5, a socket 100 that receives the user's thigh stump attaches to the four internally-threaded posts 242 on the upper surface of the residual thigh attachment plate 202 with four threaded male fasteners (not shown). The residual thigh attachment plate 202 has two lobes 248, each of which is equipped with one of a pair of spaced-apart coaxial apertures which receive a second titanium axle 200 that secures the mounting eyelet 201 of the control unit within the gap between the two lobes 248. A second set screw 244 secures the second titanium axle within the lobes 248.

A control unit (the complete assembly of FIGS. 6 and 7) provides a continual adjustable downward force on the shin frame, as well as adjustable double-acting shock absorption. The control unit, which is essentially a compressed-air-assisted MacPherson strut, includes an mounting eyelet 201 that is secured to a plunger shaft 214. An upper spring retention collar 206 slides over the plunger shaft 214, with upward movement thereof being limited by the eyelet 201. An internally-threaded trunnion mount 236 engages external threads on a main body 218, thereby enabling the vertical position of the trunnion mount 236 on the main body 218 to be adjusted. An internally-threaded lower spring retention collar 220 also engages the external threads on the main body 218, thereby enabling its vertical position to also be adjusted. An end cap 232 also engages the treads of the main body 218, thereby sealing the internal chamber of the main body.

Figure 6:
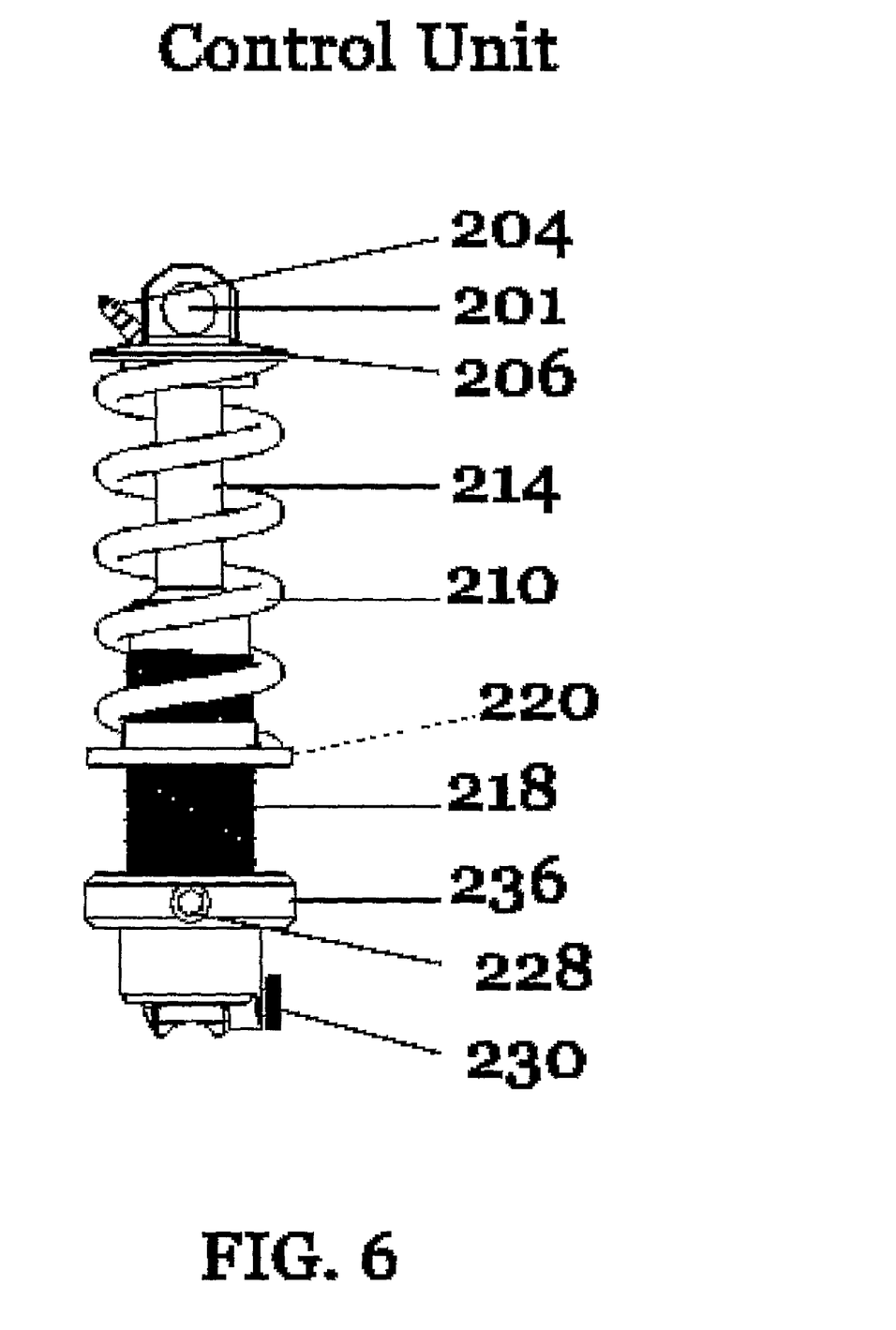
FIG. 6 is an isometric side view of the control unit component and it's parts.
Figure 7:
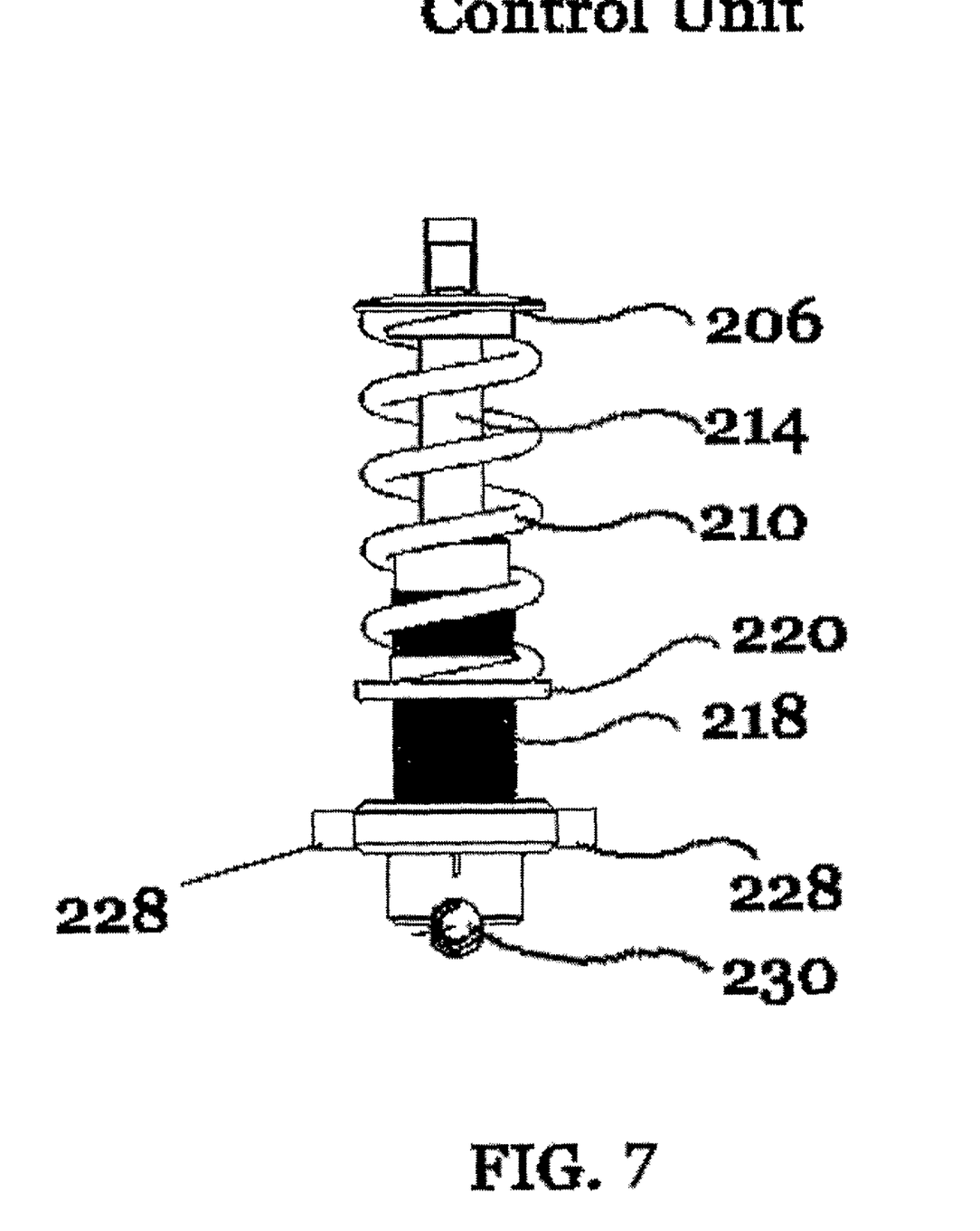
FIG. 7 is an isometric front view of the control unit component and it's parts.

The control unit is assembled by sliding the upper spring retention collar over the plunger shaft 214, inserting the end of the plunger shaft 214 opposite the mounting eyelet 201 into a sealed cylindrical aperture at the upper end of the main body 218, securing a double-acting piston to the inserted end of the plunger shaft 214 within an internal cylindrical chamber (not shown) within the main body 218, sliding the coil spring 210 over the main body 218 until it is seated against the upper spring retention collar 206, installing the lower spring retention collar 220 on the main body and tightening it against the bottom of the coil spring 210 until a desired spring preload condition is obtained, installing the trunnion mount 236 at a desired vertical location on the main body 218, filling the internal cylindrical chamber of the main body 218 with hydraulic fluid, and installing the end cap 232 and rebound adjustment knob 230 to seal the internal cylindrical chamber. The rebound adjustment knob 230 adjusts return flow of hydraulic fluid during the rebound stroke of the control unit, thereby controlling rebound speed. Preload of the control unit is controlled by the vertical position of the lower spring retention collar 220, as well as internal pressure within the internal cylindrical chamber, which can be increased by injecting compressed air through the air valve 204.

A trunnion is formed by a pair of cylindrical-head titanium socket bolts 228 that threadably engage the trunnion mount 236. The trunnion allows the lower end of the control unit to pivot within one of three pairs of apertures 222 in a lower portion of the shin frame 216. Thus, the trunnion mount 236 may be installed in one of three locations in the shin frame 222. The middle location corresponds to a normal positioning of the lower end of the control unit. When installed in the rearmost location, the control unit functions much like a compound bow, becoming less forceful at full compression due to the resulting geometry, but still ready to spring back into action. This position makes it easier for a telemark skier to stay in a turn position on steeper terrain in which his gravitational pull is not placed directly above the knee as it is on flat ground. In the foremost position, compression over the full range is much more linear giving constant tension and full rebound throughout the range of motion. This works well for activities such as snow boarding and surfing in which the user must have a stable knee at all times but be able to absorb shock and move dynamically. By adjusting the vertical position of the trunnion mount 236 with respect to the cylindrical main body 218, the distance between the trunnion (i.e., the cylindrical-head bolts 228)) and the second titanium axle 200 (which couples the mounting eyelet 201 to the residual thigh attachment plate 202) can be varied. Adjustment of this distance changes the angle that the shin frame 216 makes with the residual thigh attachment plate 202 and the user's residual thigh. The shorter the distance, the more bent the knee.

The knee component 202 is attached is positioned between a thigh component 100, via a four hole pattern secured with stainless steel threaded inserts 242, said inserts being threaded on the outside diameter allowing them to thread into the thigh/knee member and being threaded on the inside diameter allowing for the securing of attachment hardware used in combining the thigh socket and other related pieces, and an ankle 104 and foot 106 components secured to the lower shin frame 216 via a four hole pattern secured with stainless steel threaded inserts 240. The present invention is comprised of a thigh/knee plate 202, an axle 208 which passes through sealed needle bearings 246, two extended lobes 248 which secure a second axle 200 held in place by a set screw 244. The thigh/knee base plate 202 connecting to the shin frame 216 pivotally via the titanium axle 208 held in place by a set screw 238 to form a pivoting joint.

The aluminum shin frame 216 comprising two titanium stopping bolts 234 secured to threaded holes 212 in the frame, three control unit position holes 222, and a four hole pattern 240 reinforced by stainless steel threaded inserts, said inserts being threaded on the outside diameter allowing them to thread into the shin frame and being threaded on the inside diameter for the securing of attachment hardware used in combining the ankle and other related pieces.

The control unit FIG. 6 and FIG. 7 comprising an eyelet 201, an air valve 204, a spring top plate 206, a coil spring 210, a air compressed plunger shaft 214, a threaded main body 218, a spring base plate 220, a lower trunion mount 236, two titanium bolts 228, a base cap 232, a hydraulic rebound adjustment nob 230.

The knee component simulating the flexion between the thigh 100 and the lower limb components 104 and 106.

Although only a single embodiment of the invention has been disclosed herein, it will be obvious to those having ordinary skill in the art of prosthetics that changes and modifications may be made thereto without departing from the scope of the invention as hereinafter claimed.

What is claimed is:

1. A prosthetic knee and lower leg assembly comprising:
a residual thigh attachment plate;
a shin frame pivotally connected to the residual thigh attachment plate; and
a suspension strut coupled to both said residual thigh attachment plate and a lower portion of said shin frame, said suspension strut having a hydraulic chamber within an externally-threaded main body, a plunger shaft which slides within said hydraulic chamber, a coil spring which biases the plunger shaft to a fully-extended position, an air valve coupled to the hydraulic chamber for injecting compressed air into that chamber for providing additional bias on said plunger shaft, an internally-threaded spring retention collar which engages said externally-threaded main body, said internally-threaded spring retention collar enabling tension on said coil spring to be adjusted, and a trunnion unit affixed to said suspension strut for pivotally coupling the latter between said residual thigh attachment plate and said shin frame, said suspension strut dynamically storing energy as said shin frame is pivoted from an extended position to a bent position, and releasing energy as it is pivoted from the bent position to the extended position, thereby simulating the function of the quadriceps during sporting applications such as skiing, rock climbing and surfing.

2. The prosthetic knee and lower leg assembly of claim 1, wherein said residual thigh attachment plate is equipped with a first plurality of internally-threaded posts for receiving threaded fasteners which secure a thigh socket which is securable to a residual thigh of the user.

3. The prosthetic knee and lower leg assembly of claim 1, wherein said residual thigh attachment plate and said shin frame are pivotally coupled by an axle within a pair of spaced-apart sealed bearing assemblies, said bearing assemblies serving to minimize friction between the two rotatably coupled components.

4. The prosthetic knee and lower leg assembly of claim 3, wherein said sealed bearing assemblies are located within the residual thigh attachment plate, and the ends of said axle are anchored within a first set of cylindrical apertures on opposite sides of the shin frame.

5. The prosthetic knee and lower leg assembly of claim 4, wherein said residual thigh attachment plate further comprises a pair of spaced-apart lobes which are rearward projecting, each lobe having one of a second set of cylindrical apertures, both cylindrical apertures of said second set providing anchoring points for opposite ends of a pin that secures an uppermost portion of the suspension strut to said residual thigh attachment plate, said pin being secured within said second set of cylindrical apertures with at least one set screw.

6. The prosthetic knee and lower leg assembly of claim 1, wherein said shin frame is formed from a single piece of structural metal selected from the group consisting of aluminum, magnesium, and alloys thereof, said single piece being a generally channel-shaped member with a bottom panel.

7. The prosthetic knee and lower leg assembly of claim 6, wherein said bottom panel is equipped with a second plurality of threaded holes for receiving threaded fasteners which secure a prosthetic foot and ankle assembly to said shin frame.

8. The prosthetic knee and lower leg assembly of claim 1, wherein said suspension strut provides both pressurized air and spring pre-load biasing forces to resist pivoting of the shin frame from an extended position in response to an upward force being applied to a lower portion of said shin frame, said biasing acting to return said shin frame to the extended position when said upward force is reduced.

9. The prosthetic knee and lower leg assembly of claim 8, wherein said pre-load biasing can be adjusted by either adjusting a compressed length of said spring or by adjusting air pressure within said hydraulic chamber in order to accommodate different user weights, different levels of physical aggressiveness, and different physical activities.

10. The prosthetic knee and lower leg assembly of claim 1, wherein said shin frame is equipped with a plurality of discrete coupling positions for said suspension strut, each position providing a different leverage value for compression of said control unit when said shin frame is pivoted from an extended position.

11. The prosthetic knee and lower leg assembly of claim 1, wherein adjustment of the coil spring pre-load by threading the internally-threaded spring retention collar up or down on the control unit body provides for more or less pre-load, respectively, thereby providing adjustability of simulated quadricep muscle strength for different sports activities and adaptability for a users weight and aggressiveness.

12. The prosthetic knee and lower leg assembly of claim 1, wherein a pair of stopping bolts control a maximum rotation of the residual thigh attachment plate when said stopping bolts come to rest against the residual thigh attachment plate as said residual thigh attachment plate rotates around the axle.

* * * * *